US011849990B2

(12) United States Patent
Hastings et al.

(10) Patent No.: US 11,849,990 B2
(45) Date of Patent: Dec. 26, 2023

(54) VAPOR ABLATION SYSTEMS AND METHODS

(71) Applicant: NxThera, Inc., Maple Grove, MN (US)

(72) Inventors: Roger Noel Hastings, Naples, FL (US); Michael Hoey, Shoreview, MN (US); Steven Carlson, St. Paul, MN (US); Matthew Byrne, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1405 days.

(21) Appl. No.: 16/229,227

(22) Filed: Dec. 21, 2018

(65) Prior Publication Data
US 2019/0110830 A1 Apr. 18, 2019

Related U.S. Application Data

(63) Continuation of application No. 15/035,944, filed as application No. PCT/US2014/069559 on Dec. 10, 2014, now Pat. No. 10,194,970.
(Continued)

(51) Int. Cl.
*A61B 18/04* (2006.01)
*A61B 17/00* (2006.01)
A61B 18/00 (2006.01)

(52) U.S. Cl.
CPC ........ *A61B 18/04* (2013.01); *A61B 17/00234* (2013.01); *A61B 2017/00292* (2013.01);
(Continued)

(58) Field of Classification Search
CPC .............. A61B 17/00234; A61B 18/04; A61B 2017/00292; A61B 2018/00029;
(Continued)

(56) References Cited

U.S. PATENT DOCUMENTS

| 408,899 A | 8/1889 | Small |
| 1,719,750 A | 7/1929 | Bridge et al. |

(Continued)

FOREIGN PATENT DOCUMENTS

| CN | 2061443 U | 9/1990 |
| CN | 2418844 Y | 2/2001 |

(Continued)

OTHER PUBLICATIONS

US 5,326,343 A, 07/1994, Rudie et al. (withdrawn)
(Continued)

*Primary Examiner* — Jaymi E Della
(74) *Attorney, Agent, or Firm* — Bookoff McAndrews, PLLC

(57) ABSTRACT

A vapor delivery system and method is provided that includes a number of features. In one embodiment, a method comprises inserting a vapor delivery needle into tissue of a patient, activating a flow of vapor from a vapor generator through vapor delivery ports of the vapor delivery needle to cause condensed liquid to exit vapor delivery ports of the vapor delivery needle, generating vapor in the vapor generator, delivering a dose of vapor through the vapor delivery ports of the vapor delivery needle into the tissue, and after the dose of vapor is delivered, re-activating the flow of vapor from the vapor generator through the vapor delivery ports of the vapor delivery needle to prevent a vacuum from forming in the vapor delivery needle. Vapor therapy systems are also provided.

20 Claims, 7 Drawing Sheets

Related U.S. Application Data

(60) Provisional application No. 61/914,282, filed on Dec. 10, 2013.

(52) U.S. Cl.
CPC .............. *A61B 2018/00029* (2013.01); *A61B 2018/00035* (2013.01); *A61B 2018/00547* (2013.01); *A61B 2018/00577* (2013.01); *A61B 2018/00666* (2013.01); *A61B 2018/00714* (2013.01); *A61B 2018/00744* (2013.01); *A61B 2018/00755* (2013.01); *A61B 2018/00791* (2013.01); *A61B 2018/00875* (2013.01); *A61B 2018/044* (2013.01); *A61B 2018/048* (2013.01); *A61B 2218/002* (2013.01); *A61B 2218/007* (2013.01)

(58) Field of Classification Search
CPC ........... A61B 2018/00035; A61B 2018/00577; A61B 2018/00666; A61B 2018/00714; A61B 2018/00744; A61B 2018/00755; A61B 2018/00791; A61B 2018/00875; A61B 2018/044; A61B 2018/048; A61B 2218/002; A61B 2218/007; A61B 2005/1406; A61M 2005/1403
See application file for complete search history.

(56) References Cited

U.S. PATENT DOCUMENTS

| | | |
|---|---|---|
| 4,672,963 A | 6/1987 | Barken |
| 4,920,982 A | 5/1990 | Goldstein |
| 4,950,267 A | 8/1990 | Ishihara et al. |
| 5,117,482 A | 5/1992 | Hauber |
| 5,222,185 A | 6/1993 | McCord, Jr. |
| 5,249,585 A | 10/1993 | Turner et al. |
| 5,300,099 A | 4/1994 | Rudie |
| 5,312,399 A | 5/1994 | Hakky et al. |
| 5,330,518 A | 7/1994 | Neilson et al. |
| 5,366,490 A | 11/1994 | Edwards et al. |
| 5,370,609 A | 12/1994 | Drasler et al. |
| 5,370,675 A | 12/1994 | Edwards et al. |
| 5,370,677 A | 12/1994 | Rudie et al. |
| 5,385,544 A | 1/1995 | Edwards et al. |
| 5,409,453 A | 4/1995 | Lundquist et al. |
| 5,413,588 A | 5/1995 | Rudie et al. |
| 5,421,819 A | 6/1995 | Edwards et al. |
| 5,435,805 A | 7/1995 | Edwards et al. |
| 5,464,437 A | 11/1995 | Reid et al. |
| 5,470,308 A | 11/1995 | Edwards et al. |
| 5,470,309 A | 11/1995 | Edwards et al. |
| 5,484,400 A | 1/1996 | Edwards et al. |
| 5,499,998 A | 3/1996 | Meade |
| 5,531,676 A | 7/1996 | Edwards et al. |
| 5,531,763 A | 7/1996 | Mastri et al. |
| 5,542,915 A | 8/1996 | Edwards et al. |
| 5,542,916 A | 8/1996 | Hirsch et al. |
| 5,545,171 A | 8/1996 | Sharkey et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,673 A | 9/1996 | Edwards et al. |
| 5,588,960 A | 12/1996 | Edwards et al. |
| 5,591,125 A | 1/1997 | Edwards et al. |
| 5,599,294 A | 2/1997 | Edwards et al. |
| 5,601,591 A | 2/1997 | Edwards et al. |
| 5,628,770 A | 5/1997 | Thome et al. |
| 5,630,794 A | 5/1997 | Lax et al. |
| 5,645,528 A | 7/1997 | Thome |
| 5,667,488 A | 9/1997 | Lundquist et al. |
| 5,672,153 A | 9/1997 | Lax et al. |
| 5,709,680 A | 1/1998 | Yates et al. |
| 5,720,718 A | 2/1998 | Rosen et al. |
| 5,720,719 A | 2/1998 | Edwards et al. |
| 5,776,176 A | 7/1998 | Rudie |
| 5,792,070 A | 8/1998 | Kauphusman et al. |
| 5,797,903 A | 8/1998 | Swanson et al. |
| 5,800,486 A | 9/1998 | Thome et al. |
| 5,807,395 A | 9/1998 | Mulier et al. |
| 5,830,179 A | 11/1998 | Mikus et al. |
| 5,843,144 A | 12/1998 | Rudie et al. |
| 5,849,011 A | 12/1998 | Jones et al. |
| 5,861,021 A | 1/1999 | Thome et al. |
| 5,871,481 A | 2/1999 | Kannenberg et al. |
| 5,873,877 A | 2/1999 | McGaffigan et al. |
| 5,897,553 A | 4/1999 | Mulier et al. |
| 5,899,932 A | 5/1999 | Dann et al. |
| 5,938,692 A | 8/1999 | Rudie |
| 5,944,715 A | 8/1999 | Goble et al. |
| 5,951,515 A | 9/1999 | Osterlind |
| 5,957,922 A | 9/1999 | Imran |
| 5,964,752 A | 10/1999 | Stone |
| 5,964,756 A | 10/1999 | McGaffigan et al. |
| 5,976,123 A | 11/1999 | Baumgardner et al. |
| 5,987,360 A | 11/1999 | McGrath et al. |
| 5,990,465 A | 11/1999 | Nakaoka et al. |
| 6,007,571 A | 12/1999 | Neilson et al. |
| 6,009,351 A | 12/1999 | Flachman |
| 6,017,358 A | 1/2000 | Yoon et al. |
| 6,017,361 A | 1/2000 | Mikus et al. |
| 6,036,631 A | 3/2000 | McGrath et al. |
| 6,036,713 A | 3/2000 | Kieturakis |
| 6,053,909 A | 4/2000 | Shadduck |
| 6,063,081 A | 5/2000 | Mulier et al. |
| 6,067,475 A | 5/2000 | Graves et al. |
| 6,077,257 A | 6/2000 | Edwards et al. |
| 6,113,593 A | 9/2000 | Tu et al. |
| 6,122,551 A | 9/2000 | Rudie et al. |
| 6,123,083 A | 9/2000 | McGrath et al. |
| 6,147,336 A | 11/2000 | Oshijima et al. |
| 6,148,236 A | 11/2000 | Dann |
| 6,156,036 A | 12/2000 | Sussman et al. |
| 6,161,049 A | 12/2000 | Rudie et al. |
| 6,179,805 B1 | 1/2001 | Sussman et al. |
| 6,179,836 B1 | 1/2001 | Eggers et al. |
| 6,206,847 B1 | 3/2001 | Edwards et al. |
| 6,210,404 B1 | 4/2001 | Shadduck |
| 6,223,085 B1 | 4/2001 | Dann et al. |
| 6,231,591 B1 | 5/2001 | Desai |
| 6,235,022 B1 | 5/2001 | Hallock et al. |
| 6,238,389 B1 | 5/2001 | Paddock et al. |
| 6,238,391 B1 | 5/2001 | Olsen et al. |
| 6,238,393 B1 | 5/2001 | Mulier et al. |
| 6,241,702 B1 | 6/2001 | Lundquist et al. |
| 6,258,087 B1 | 7/2001 | Edwards et al. |
| 6,272,384 B1 | 8/2001 | Simon et al. |
| 6,287,297 B1 | 9/2001 | Woodruff et al. |
| 6,302,903 B1 | 10/2001 | Mulier et al. |
| 6,312,391 B1 | 11/2001 | Ramadhyani et al. |
| 6,315,777 B1 | 11/2001 | Comben |
| 6,348,039 B1 | 2/2002 | Flachman et al. |
| 6,398,759 B1 | 6/2002 | Sussman et al. |
| 6,409,722 B1 | 6/2002 | Hoey et al. |
| 6,423,027 B1 | 7/2002 | Gonon |
| 6,440,127 B2 | 8/2002 | McGovern et al. |
| 6,461,296 B1 | 10/2002 | Desai |
| 6,494,902 B2 | 12/2002 | Hoey et al. |
| 6,496,737 B2 | 12/2002 | Rudie et al. |
| 6,508,816 B2 | 1/2003 | Shadduck |
| 6,517,534 B1 | 2/2003 | McGovern et al. |
| 6,524,270 B1 | 2/2003 | Bolmsjo et al. |
| 6,537,248 B2 | 3/2003 | Mulier et al. |
| 6,537,272 B2 | 3/2003 | Christopherson et al. |
| 6,544,211 B1 | 4/2003 | Andrew et al. |
| 6,551,300 B1 | 4/2003 | McGaffigan |
| 6,565,561 B1 | 5/2003 | Goble et al. |
| 6,575,929 B2 | 6/2003 | Sussman et al. |
| 6,575,968 B1 | 6/2003 | Eggers et al. |
| 6,579,270 B2 | 6/2003 | Sussman et al. |
| 6,589,201 B1 | 7/2003 | Sussman et al. |
| 6,607,529 B1 | 8/2003 | Jones et al. |
| 6,638,275 B1 | 10/2003 | McGaffigan et al. |
| 6,640,139 B1 | 10/2003 | Ueberle |

(56) References Cited

U.S. PATENT DOCUMENTS

| | | |
|---|---|---|
| 6,669,694 B2 | 12/2003 | Shadduck |
| 6,676,628 B2 | 1/2004 | Sussman et al. |
| 6,706,039 B2 | 3/2004 | Mulier et al. |
| 6,716,252 B2 | 4/2004 | Lazarovitz et al. |
| 6,719,738 B2 | 4/2004 | Mehier |
| 6,726,696 B1 | 4/2004 | Houser et al. |
| 6,730,079 B2 | 5/2004 | Lovewell |
| 6,736,810 B2 | 5/2004 | Hoey et al. |
| 6,740,108 B1 | 5/2004 | Just et al. |
| 6,760,616 B2 | 7/2004 | Hoey et al. |
| 6,780,178 B2 | 8/2004 | Palanker et al. |
| 6,794,455 B2 | 9/2004 | Hung et al. |
| 6,827,718 B2 | 12/2004 | Hutchins et al. |
| 6,855,141 B2 | 2/2005 | Lovewell |
| 6,887,237 B2 | 5/2005 | McGaffigan |
| 6,905,475 B2 | 6/2005 | Hauschild et al. |
| 6,911,028 B2 | 6/2005 | Shadduck |
| 6,969,376 B2 | 11/2005 | Takagi et al. |
| 7,014,652 B2 | 3/2006 | Cioanta et al. |
| 7,041,121 B1 | 5/2006 | Williams et al. |
| 7,066,935 B2 | 6/2006 | Swoyer et al. |
| 7,089,064 B2 | 8/2006 | Manker et al. |
| 7,130,697 B2 | 10/2006 | Chomenky et al. |
| 7,238,182 B2 | 7/2007 | Swoyer et al. |
| 7,247,155 B2 | 7/2007 | Hoey et al. |
| 7,261,709 B2 | 8/2007 | Swoyer et al. |
| 7,261,710 B2 | 8/2007 | Elmouelhi et al. |
| 7,322,974 B2 | 1/2008 | Swoyer et al. |
| 7,328,068 B2 | 2/2008 | Spinelli et al. |
| 7,328,069 B2 | 2/2008 | Gerber |
| 7,335,197 B2 | 2/2008 | Sage et al. |
| 7,340,300 B2 | 3/2008 | Christopherson et al. |
| 7,369,894 B2 | 5/2008 | Gerber |
| 7,429,262 B2 | 9/2008 | Woloszko et al. |
| 7,437,194 B2 | 10/2008 | Swarek et al. |
| 7,470,228 B2 | 12/2008 | Connors et al. |
| 7,549,987 B2 | 6/2009 | Shadduck |
| 7,865,250 B2 | 1/2011 | Mrva et al. |
| 7,894,913 B2 | 2/2011 | Boggs et al. |
| 7,959,577 B2 | 6/2011 | Schmitz et al. |
| 8,048,069 B2 | 11/2011 | Skwarek et al. |
| 8,216,217 B2 | 7/2012 | Sharkey et al. |
| 8,244,327 B2 | 8/2012 | Fichtinger et al. |
| 8,251,985 B2 | 8/2012 | Hoey et al. |
| 8,272,383 B2 | 9/2012 | Hoey et al. |
| 8,273,079 B2 | 9/2012 | Hoey et al. |
| 8,301,264 B2 | 10/2012 | Achenbach et al. |
| 8,313,485 B2 | 11/2012 | Shadduck |
| 8,372,065 B2 | 2/2013 | Hoey et al. |
| 8,388,611 B2 | 3/2013 | Shadduck et al. |
| 8,409,109 B2 | 4/2013 | Tiesma et al. |
| 8,419,723 B2 | 4/2013 | Shadduck et al. |
| 8,550,743 B2 | 10/2013 | Bonde et al. |
| 8,585,692 B2 | 11/2013 | Shadduck et al. |
| 8,632,530 B2 | 1/2014 | Hoey et al. |
| 8,740,957 B2 | 6/2014 | Masotti |
| 8,801,702 B2 | 8/2014 | Hoey et al. |
| 8,900,223 B2 | 12/2014 | Shadduck |
| 9,198,708 B2 | 12/2015 | Hoey et al. |
| 9,345,507 B2 | 5/2016 | Hoey et al. |
| 2002/0078956 A1 | 6/2002 | Sharpe et al. |
| 2002/0111617 A1 | 8/2002 | Cosman et al. |
| 2002/0177846 A1 | 11/2002 | Mulier et al. |
| 2003/0069575 A1 | 4/2003 | Chin et al. |
| 2003/0092689 A1 | 5/2003 | Escandon et al. |
| 2003/0097126 A1 | 5/2003 | Woloszko et al. |
| 2003/0130575 A1 | 7/2003 | Desai |
| 2003/0206730 A1 | 11/2003 | Golan |
| 2004/0006334 A1 | 1/2004 | Beyar et al. |
| 2004/0068306 A1 | 4/2004 | Shadduck |
| 2004/0186422 A1 | 9/2004 | Rioux et al. |
| 2004/0230316 A1 | 11/2004 | Cioanta et al. |
| 2004/0267340 A1 | 12/2004 | Cioanta et al. |
| 2005/0096629 A1 | 5/2005 | Gerber et al. |
| 2005/0124915 A1 | 6/2005 | Eggers et al. |
| 2005/0149020 A1 | 7/2005 | Jahng |
| 2005/0159676 A1 | 7/2005 | Taylor et al. |
| 2005/0273090 A1* | 12/2005 | Nieman ............... A61B 18/14 606/17 |
| 2006/0089636 A1 | 4/2006 | Christopherson et al. |
| 2006/0135955 A1 | 6/2006 | Shadduck |
| 2006/0178670 A1 | 8/2006 | Woloszko et al. |
| 2006/0224154 A1 | 10/2006 | Shadduck et al. |
| 2006/0224169 A1 | 10/2006 | Weisenburgh, II et al. |
| 2006/0253069 A1 | 11/2006 | Li et al. |
| 2006/0276871 A1 | 12/2006 | Lamson et al. |
| 2007/0032785 A1 | 2/2007 | Diederich et al. |
| 2007/0038089 A1 | 2/2007 | Hatano et al. |
| 2007/0142846 A1 | 6/2007 | Catanese, III et al. |
| 2007/0179491 A1 | 8/2007 | Kratoska et al. |
| 2007/0197864 A1 | 8/2007 | Dejima et al. |
| 2007/0213703 A1 | 9/2007 | Naam et al. |
| 2008/0021484 A1 | 1/2008 | Catanese, III et al. |
| 2008/0021485 A1 | 1/2008 | Catanese, III et al. |
| 2008/0033232 A1 | 2/2008 | Catanese, III et al. |
| 2008/0033458 A1 | 2/2008 | McLean et al. |
| 2008/0033488 A1 | 2/2008 | Catanese, III et al. |
| 2008/0039833 A1 | 2/2008 | Catanese, III et al. |
| 2008/0039872 A1 | 2/2008 | Catanese, III et al. |
| 2008/0039874 A1 | 2/2008 | Catanese, III et al. |
| 2008/0039875 A1 | 2/2008 | Catanese, III et al. |
| 2008/0039876 A1 | 2/2008 | Catanese, III et al. |
| 2008/0039893 A1 | 2/2008 | McLean et al. |
| 2008/0039894 A1 | 2/2008 | Catanese, III et al. |
| 2008/0046045 A1 | 2/2008 | Yon et al. |
| 2008/0110457 A1 | 5/2008 | Barry et al. |
| 2008/0132826 A1 | 6/2008 | Shadduck et al. |
| 2008/0188811 A1 | 8/2008 | Kim |
| 2008/0208187 A1 | 8/2008 | Bhushan et al. |
| 2008/0214956 A1 | 9/2008 | Briggs et al. |
| 2008/0217325 A1 | 9/2008 | Von Buren et al. |
| 2008/0249399 A1 | 10/2008 | Appling et al. |
| 2008/0262491 A1 | 10/2008 | Swoyer et al. |
| 2008/0269737 A1 | 10/2008 | Elmouelhi et al. |
| 2008/0269862 A1 | 10/2008 | Elmouelhi et al. |
| 2008/0275440 A1 | 11/2008 | Kratoska et al. |
| 2008/0297287 A1 | 12/2008 | Shachar et al. |
| 2008/0312497 A1 | 12/2008 | Elmouelhi et al. |
| 2009/0018553 A1 | 1/2009 | McLean et al. |
| 2009/0054871 A1 | 2/2009 | Sharkey et al. |
| 2009/0138001 A1 | 5/2009 | Barry et al. |
| 2009/0149846 A1* | 6/2009 | Hoey ............... A61M 25/10 606/27 |
| 2009/0199855 A1 | 8/2009 | Davenport |
| 2009/0216220 A1 | 8/2009 | Hoey et al. |
| 2009/0227998 A1 | 9/2009 | Aljuri et al. |
| 2009/0306640 A1 | 12/2009 | Glaze et al. |
| 2010/0016757 A1 | 1/2010 | Greenburg et al. |
| 2010/0049031 A1 | 2/2010 | Fruland et al. |
| 2010/0094270 A1* | 4/2010 | Sharma ............... A61B 17/24 604/523 |
| 2010/0114083 A1 | 5/2010 | Sharma |
| 2010/0179416 A1 | 7/2010 | Hoey et al. |
| 2010/0193568 A1 | 8/2010 | Scheib et al. |
| 2010/0204688 A1 | 8/2010 | Hoey et al. |
| 2010/0256636 A1 | 10/2010 | Fernandez et al. |
| 2010/0262133 A1 | 10/2010 | Hoey et al. |
| 2010/0262137 A1 | 10/2010 | Nye et al. |
| 2010/0286679 A1 | 11/2010 | Hoey et al. |
| 2010/0292767 A1 | 11/2010 | Hoey et al. |
| 2010/0298948 A1 | 11/2010 | Hoey et al. |
| 2011/0060328 A1 | 3/2011 | Skwarek et al. |
| 2011/0077628 A1 | 3/2011 | Hoey et al. |
| 2011/0106072 A1 | 5/2011 | Sundquist et al. |
| 2011/0160648 A1 | 6/2011 | Hoey |
| 2011/0264176 A1* | 10/2011 | Jackson ............... A61B 18/04 607/105 |
| 2011/0319759 A1 | 12/2011 | Liu et al. |
| 2012/0259271 A1 | 10/2012 | Shadduck et al. |
| 2012/0265276 A1 | 10/2012 | Curley |
| 2012/0323167 A1 | 12/2012 | Hoey et al. |
| 2013/0006231 A1 | 1/2013 | Sharma et al. |
| 2013/0066308 A1 | 3/2013 | Landman |
| 2013/0072855 A1 | 3/2013 | Sherry et al. |

(56) References Cited

U.S. PATENT DOCUMENTS

| | | |
|---|---|---|
| 2013/0074847 A1 | 3/2013 | Hoey et al. |
| 2013/0172867 A1 | 7/2013 | Shadduck et al. |
| 2013/0261692 A1 | 10/2013 | Cardinal et al. |
| 2014/0039356 A1 | 2/2014 | Sachs et al. |
| 2014/0200568 A1 | 7/2014 | Sharma |
| 2014/0276713 A1 | 9/2014 | Hoey et al. |
| 2014/0288543 A1 | 9/2014 | Hoey et al. |
| 2014/0354381 A1 | 12/2014 | Kohlhafer |
| 2015/0025515 A1 | 1/2015 | Hoey et al. |
| 2015/0126990 A1 | 5/2015 | Sharma et al. |
| 2015/0157384 A1 | 6/2015 | Hoey et al. |
| 2016/0015445 A1 | 1/2016 | Hoey et al. |
| 2016/0081736 A1 | 3/2016 | Hoey et al. |
| 2017/0056089 A1 | 3/2017 | Hoey et al. |
| 2018/0168711 A1 | 6/2018 | Hoey et al. |
| 2018/0168712 A1 | 6/2018 | Hoey et al. |
| 2018/0193080 A1 | 7/2018 | Hoey et al. |

FOREIGN PATENT DOCUMENTS

| | | |
|---|---|---|
| CN | 101072544 | 11/2007 |
| CN | 101257855 | 9/2008 |
| CN | 101006939 A | 11/2008 |
| CN | 101491458 A | 7/2009 |
| CN | 101803947 A | 8/2010 |
| JP | 7-507696 A | 8/1995 |
| JP | 8-501957 A | 3/1996 |
| JP | 8-504613 A | 5/1996 |
| JP | 11-318925 A | 11/1999 |
| JP | 200014663 A | 1/2000 |
| JP | 20000005191 A | 1/2000 |
| JP | 2001500763 A | 1/2001 |
| JP | 2005137916 A | 6/2005 |
| WO | 92/10142 A1 | 6/1992 |
| WO | 01/24715 A1 | 4/2001 |
| WO | 03/088851 A1 | 10/2003 |
| WO | 2003/096871 A2 | 11/2003 |
| WO | 2005/102416 A1 | 11/2005 |
| WO | 2006/004482 A1 | 1/2006 |
| WO | 2008/083407 A1 | 7/2008 |
| WO | 2010080467 A2 | 7/2010 |
| WO | 2013/160772 A2 | 10/2013 |
| WO | 2017/106843 A1 | 6/2017 |

OTHER PUBLICATIONS

Hai; Photoselective Vaporization Prostatectomy: A Palliative Treatment Option for Men with Urinary Obstruction Secondary to Prostate Cancer; PCRI Prost. Cancer Rsrch.Inst. Reprint.from PCRI Insights Nov. 2005, vol. 8(4); Dwnld from http://www.prostate-cancer.org/pcricms/node/233 on May 10, 2012; 4 pages.

Nguyen et al; Updated results of magnetic resonance imaging guided partial prostate brachytherapy for favorable risk prostate cancer: implications for focal therapy; J. Urol.; 188(4); pp. 1151-1156; Oct. 2012.

Hastings et al.; U.S. Appl. No. 15/011,005 entitled "Vapor ablation systems and methods," filed Jan. 29, 2016.

Hoey et al.; U.S. Appl. No. 15/154,536 entitled "Systems and methods for treating the bladder with condensable vapor," filed May 13, 2016.

\* cited by examiner

VAPOR ABLATION SYSTEMS AND METHODS

CROSS REFERENCE TO RELATED APPLICATIONS

This application is a continuation under 37 CFR § 1.53(b) of U.S. application Ser. No. 15/035,944, which has a § 371(c) date of May 11, 2016, issued as U.S. Pat. No. 10,194,970 on Feb. 5, 2019, which is a national stage filing under 35 U.S.C. § 371 of International Application No. PCT/US2014/069559, filed Dec. 10, 2014, which claims the benefit of U.S. Provisional Patent Application No. 61/914,282, filed Dec. 10, 2013, titled "VAPOR ABLATION SYSTEMS AND METHODS", each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates to devices and related methods for treatment of benign prostatic hyperplasia using a minimally invasive approach.

BACKGROUND

Benign prostatic hyperplasia (BPH) is a common disorder in middle-aged and older men, with prevalence increasing with age. At age 50, more than one-half of men have symptomatic BPH, and by age 70, nearly 90% of men have microscopic evidence of an enlarged prostate. The severity of symptoms also increase with age with 27% of patients in the 60-70 age bracket having moderate-to-severe symptoms, and 37% of patients in their 70's suffering from moderate-to-severe symptoms.

The prostate early in life is the size and shape of a walnut and prior to the enlargement resulting from BPH, weighs about 20 grams. Prostate enlargement appears to be a normal process. With age, the prostate gradually increases in size to twice or more its normal size. The fibromuscular tissue of the outer prostatic capsule restricts expansion after the gland reaches a certain size. Because of such restriction on expansion, the intracapsular tissue will compress against and constrict the prostatic urethra, thus causing resistance to urine flow.

In the male urogenital anatomy, the prostate gland is located below the bladder and the bladder neck. The walls of the bladder can expand and contract to cause urine flow through the urethra, which extends from the bladder, through the prostate and penis. The portion of urethra that is surrounded by the prostate gland is referred to as the prostatic urethra. The prostate also surrounds the ejaculatory ducts which have an open termination in the prostatic urethra. During sexual arousal, sperm is transported from the testes by the ductus deferens to the prostate which provides fluids that combine with sperm to form semen during ejaculation. On each side of the prostate, the ductus deferens and seminal vesicles join to form a single tube called an ejaculatory duct. Thus, each ejaculatory duct carries the seminal vesicle secretions and sperm into the prostatic urethra.

The prostate glandular structure can be classified into three zones: the peripheral zone, transition zone, and central zone. Peripheral zone PZ comprises about 70% of the volume of a young man's prostate. This sub-capsular portion of the posterior aspect of the prostate gland surrounds the distal urethra and 70 to 80% of cancers originate in the peripheral zone tissue. The central zone CZ surrounds the ejaculatory ducts and contains about 20-25% of the prostate volume. The central zone is often the site of inflammatory processes. The transition zone TZ is the site in which benign prostatic hyperplasia develops, and contains about 5-10% of the volume of glandular elements in a normal prostate, but can constitute up to 80% of such volume in cases of BPH. The transition zone consists of two lateral prostate lobes and the periurethral gland region. There are natural barriers around the transition zone, i.e., the prostatic urethra, the anterior fibromuscular stroma, and a fibrous plane between the transition zone and peripheral zone. The anterior fibromuscular stroma or fibromuscular zone is predominantly fibromuscular tissue.

BPH is typically diagnosed when the patient seeks medical treatment complaining of bothersome urinary difficulties. The predominant symptoms of BPH are an increase in frequency and urgency of urination, and a significant decrease in the rate of flow during urination. BPH can also cause urinary retention in the bladder which in turn can lead to lower urinary tract infection (LUTI). In many cases, the LUTI then can ascend into the kidneys and cause chronic pyelonephritis, and can eventually lead to renal insufficiency. BPH also may lead to sexual dysfunction related to sleep disturbance or psychological anxiety caused by severe urinary difficulties. Thus, BPH can significantly alter the quality of life with aging of the male population.

BPH is the result of an imbalance between the continuous production and natural death (apoptosis) of the glandular cells of the prostate. The overproduction of such cells leads to increased prostate size, most significantly in the transition zone which traverses the prostatic urethra.

In early stage cases of BPH, pharmacological treatments can alleviate some of the symptoms. For example, alpha-blockers treat BPH by relaxing smooth muscle tissue found in the prostate and the bladder neck, which may allow urine to flow out of the bladder more easily. Such drugs can prove effective until the glandular elements cause overwhelming cell growth in the prostate.

More advanced stages of BPH, however, can only be treated by surgical or less-invasive thermal ablation device interventions. A number of methods have been developed using electrosurgical or mechanical extraction of tissue, and thermal ablation or cryoablation of intracapsular prostatic tissue. In many cases, such interventions provide only transient relief; and these treatments often cause significant peri-operative discomfort and morbidity.

In one thermal ablation method, RF energy is delivered to prostate tissue via an elongated RF needle being penetrated into a plurality of locations in a prostate lobe. The elongated RF needle is typically about 20 mm in length, together with an insulator that penetrates into the lobe. The resulting RF treatment thus ablates tissue away from the prostatic urethra and does not target tissue close to, and parallel to, the prostatic urethra. The application of RF energy typically extends for 1 to 3 minutes or longer which allows thermal diffusion of the RF energy to ablate tissue out to the capsule periphery. Such RF energy delivery methods may not create a durable effect, since smooth muscle tissue and alpha adrenergic receptors are not uniformly ablated around the prostatic urethra or within the transition zone. As a result, tissue in the prostate lobes can continue to grow and impinge on the urethra thus limiting long-term effectiveness of the treatment.

SUMMARY OF THE DISCLOSURE

A method for providing vapor therapy is described, comprising inserting a vapor delivery needle into tissue of a patient, activating a flow of vapor from a vapor generator through vapor delivery ports of the vapor delivery needle to cause condensed liquid to exit vapor delivery ports of the vapor delivery needle, generating vapor in the vapor generator, delivering a dose of vapor through the vapor delivery ports of the vapor delivery needle into the tissue, and after the dose of vapor is delivered, re-activating the flow of vapor from the vapor generator through the vapor delivery ports of the vapor delivery needle to prevent a vacuum from forming in the vapor delivery needle.

In some embodiments, the generating step further heating a heating element that surrounds a flow of fluid to inductively generate the vapor.

In one embodiment, the method further comprises monitoring a parameter of the heating element with an electronic controller, and controlling the parameter at a set value with the electronic controller to insure consistent caloric content of the delivered vapor. In some embodiments, the parameter is a temperature of the heating element. In another embodiment, the parameter is an electrical impedance of the heating element. In an additional embodiment, the parameter is controlled to a first set point during the delivering step and controlled to a second set point during the activating and re-activating steps.

In some embodiments, the flow of vapor in the activating and re-activating steps comprises a flow of vapor ranging from approximately 0.1-0.3 ml/min.

In another embodiment, the inserting step comprises inserting the vapor delivery needle transurethrally into a prostate of the patient.

A vapor delivery system is also provided, comprising an elongate shaft configured to be inserted into a urethra of a patient, a vapor delivery needle comprising a plurality of vapor delivery ports, the vapor delivery needle being disposed within the elongate shaft and configured to be advanced generally transverse from the elongate shaft into a prostate of the patient when the elongate shaft is positioned within the urethra of the patient, a vapor generator coupled to the vapor delivery needle through vapor delivery ports of the vapor delivery needle to cause condensed liquid to exit vapor delivery ports of the vapor delivery needle, and an electronic controller operatively coupled to the vapor generator, the electronic controller being configured to activate a flow of vapor from the vapor generator through the vapor delivery ports of the vapor delivery needle to cause condensed liquid to exit the vapor delivery ports of the vapor delivery needle, deliver a dose of vapor from the vapor generator through the vapor delivery ports of the vapor delivery needle into the prostate, and after the dose of vapor is delivered, re-activate the flow of vapor from the vapor generator through the vapor delivery needle to prevent a vacuum from forming in the vapor delivery needle.

In some embodiments, the vapor generator comprises an inductive vapor generator with a heating element surrounding a flow of fluid.

In other embodiments, the electronic controller is further configured to monitor a parameter of the heating element and control the parameter at a set value to insure consistent caloric content of the delivered vapor.

In one embodiment, the parameter is a temperature of the heating element.

In another embodiment, the parameter is an electrical impedance of the heating element.

In some embodiments, the parameter is controlled to a first set point when the electronic controller delivers the dose of vapor, and wherein the parameter is controlled to a second set point when the electronic controller activates and re-activates the flow of vapor.

In another embodiment, the flow of vapor comprises a flow of vapor ranging from approximately 0.1-0.3 ml/min.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

DETAILED DESCRIPTION OF THE INVENTION

In general, one method for treating BPH comprises introducing a heated vapor interstitially into the interior of a prostate, wherein the vapor controllably ablates prostate tissue. This method can utilize vapor for applied thermal energy of between 50 calories and 300 calories per each individual vapor treatment (and assumes multiple treatments for each prostate lobe) in an office-based procedure. The method can cause localized ablation of prostate tissue, and more particularly the applied thermal energy from vapor can be localized to ablate tissue adjacent the urethra without damaging prostate tissue that is not adjacent the urethra.

The present disclosure is directed to the treatment of BPH, and more particularly for ablating transitional zone prostate tissue without ablating central or peripheral zone prostate tissue. In one embodiment, the present disclosure is directed to treating a prostate using convective heating in a region adjacent the prostatic urethra. The method of ablative treatment is configured to target smooth muscle tissue, alpha adrenergic receptors, sympathetic nerve structures and vasculature parallel to the prostatic urethra between the bladder neck region and the verumontanum region to a depth of less than 2 cm.

The system can include a vapor delivery mechanism that delivers vapor media, including water vapor. The system can utilize a vapor source configured to provide vapor having a temperature of at least 60-140° C. In another embodiment, the system further comprises a computer controller configured to deliver vapor for an interval ranging from 1 second to 30 seconds.

In some embodiments, the system further comprises a source of a pharmacologic agent or other chemical agent or compound for delivery with the vapor. These agents include, without limitation, an anesthetic, an antibiotic or a toxin such as Botox®, or a chemical agent that can treat cancerous tissue cells. The agent also can be a sealant, an adhesive, a glue, a superglue or the like.

Figure 1:
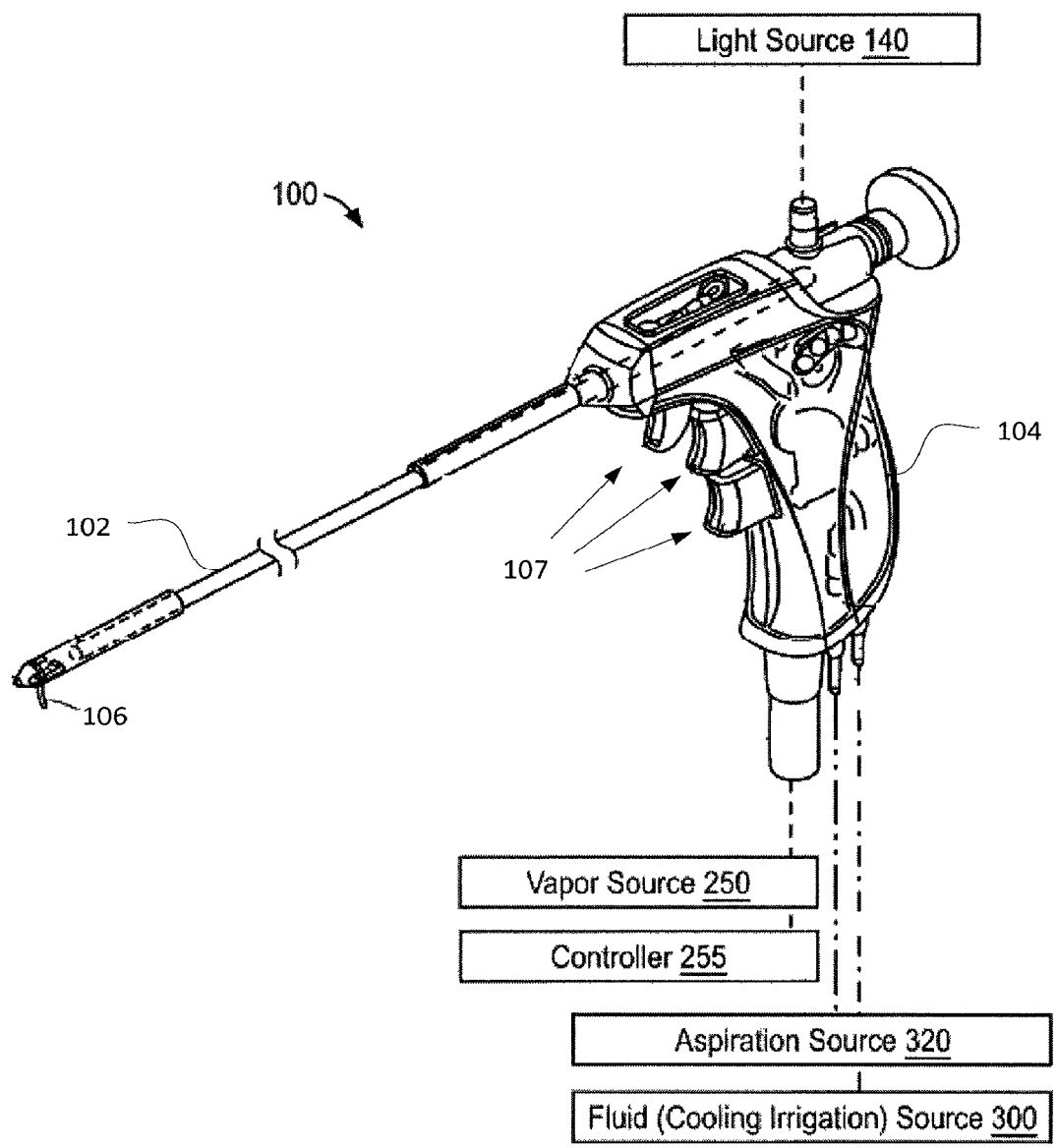
FIG. 1 shows one embodiment of a vapor delivery system.

FIG. 1 shows one embodiment of a vapor delivery system. Vapor delivery system 100 can have an elongate shaft 102 configured for insertion into the urethra of a patient and a handle portion 104 for gripping with a human hand. The vapor system 100 can include a vapor delivery needle 106 configured to extend from a distal portion of the elongate shaft 102. In some embodiments, the vapor delivery needle 106 can be retracted within the shaft during insertion of the shaft into the urethra of the patient, and the vapor delivery needle can then be advanced from the shaft into the prostate tissue when the system is properly placed within the patient. In one embodiment, the vapor delivery needle extends outwards in a generally perpendicular direction to the elongate shaft. The vapor delivery needle can extend generally perpendicular to or transverse from the shaft, and can include one or more vapor delivery ports configured to deliver a flow of vapor media from a vapor source 250 through the vapor delivery needle 106 into prostate tissue. The vapor delivery needle can further include an aspiration source 320 configured to aspirate tissue and/or fluids from the patient (e.g., either through the vapor delivery ports or through separate aspiration ports in the vapor delivery needle), and can also include a fluid source 300 configured to deliver a fluid or cooling irrigation to the tissue before, during, and/or after vapor delivery.

The vapor delivery system 100 of FIG. 1 can include a plurality of actuation mechanisms 107, such as triggers, buttons, or levers, configured to actuate the various functions of the system. For example, the actuation mechanism can be configured to extend/retract the vapor delivery needle, and start/stop the flow of vapor, aspiration, and/or the cooling irrigation.

Vapor source 250 is provided for delivering a vapor media through the vapor delivery needle to ablate tissue. The vapor source can be a vapor generator that can deliver a vapor media, such as water vapor, that has a precisely controlled quality to provide a precise amount of thermal energy delivery, for example measured in calories per second. In some embodiments, the vapor source can comprise an inductive heating system similar in which a flow media is inductively heated to generate a condensable vapor. The controller 255 can be set to control the various parameters of vapor delivery, for example, the controller can be set to delivery vapor media for a selected treatment interval, a selected pressure, or selected vapor quality. Further details on the vapor delivery system, the vapor generator, and how vapor and fluid are delivered to tissue can be found in U.S. Pat. No. 8,273,079 and PCT Publication No. WO 2013/040209, both of which are incorporated by reference. In some embodiments, the electronic controller can also control the aspiration and/or cooling irrigation functions of the vapor delivery system.

Figure 2:
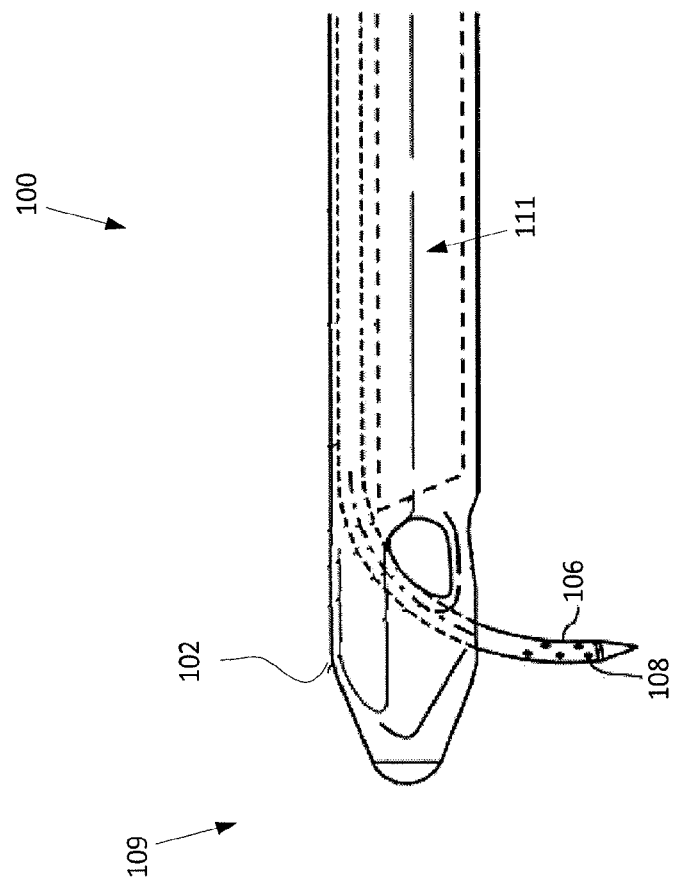
FIG. 2 is a close-up view of a distal portion of the vapor delivery system.

FIG. 2 shows a close-up view of a distal portion 109 of the shaft of vapor delivery system 100, including the vapor delivery needle 106 extending beyond the shaft and exposing the vapor delivery ports 108. The vapor delivery system 100 can further include one or more lumens 111 sized to accommodate an endoscope or camera to provide additional viewing and feedback to the physician during use. This endoscope or camera can provide a view of the distal portion of the shaft, including a view of the vapor delivery needle when deployed and inserted into tissue.

As described above in reference to FIG. 1, the vapor delivery system can be connected to a vapor source 250, an aspiration source 320, a fluid or irrigation source 300, a light source 140, and an electronic controller 255 configured to control generation and delivery of vapor from the vapor source, through a lumen of the shaft, through the vapor delivery needle, and into tissue. In some embodiments, the electronic controller can be disposed on or in the vapor delivery system, and in other embodiments the electronic controller can be disposed separate from the system. The fluid or irrigation source can provide a fluid, such as saline, through a separate lumen in the shaft to provide irrigation and flushing to tissue during insertion of the system and during vapor delivery to tissue. In some embodiments, the irrigation can be used to clear blood and debris from tissue lumens to increase visibility. The irrigation can also provide cooling to the urethra of the patient, both via direct contact of the irrigation fluid with the urethra as well as cooling the shaft of the vapor delivery system as the fluid flows from the irrigation source through the shaft and into contact with the tissue. Urethral flush can be used during the lesion formation. In one embodiment, the flush rate can be approximately 80 mL/minute, or ranging from 20 to 400 mL/minute. Changes in flush rate will change the amount of tissue cooling (depth) into the urethra and prostate, which can affect lesion size.

Figure 3:
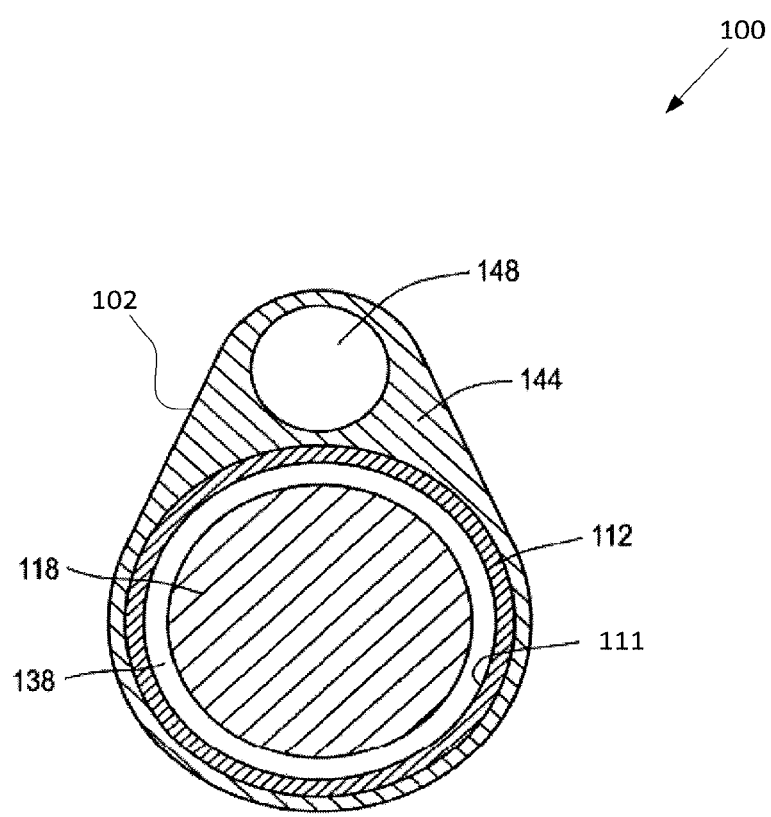
FIG. 3 is a cross-sectional view of a shaft of the vapor delivery system.
Figure 4:
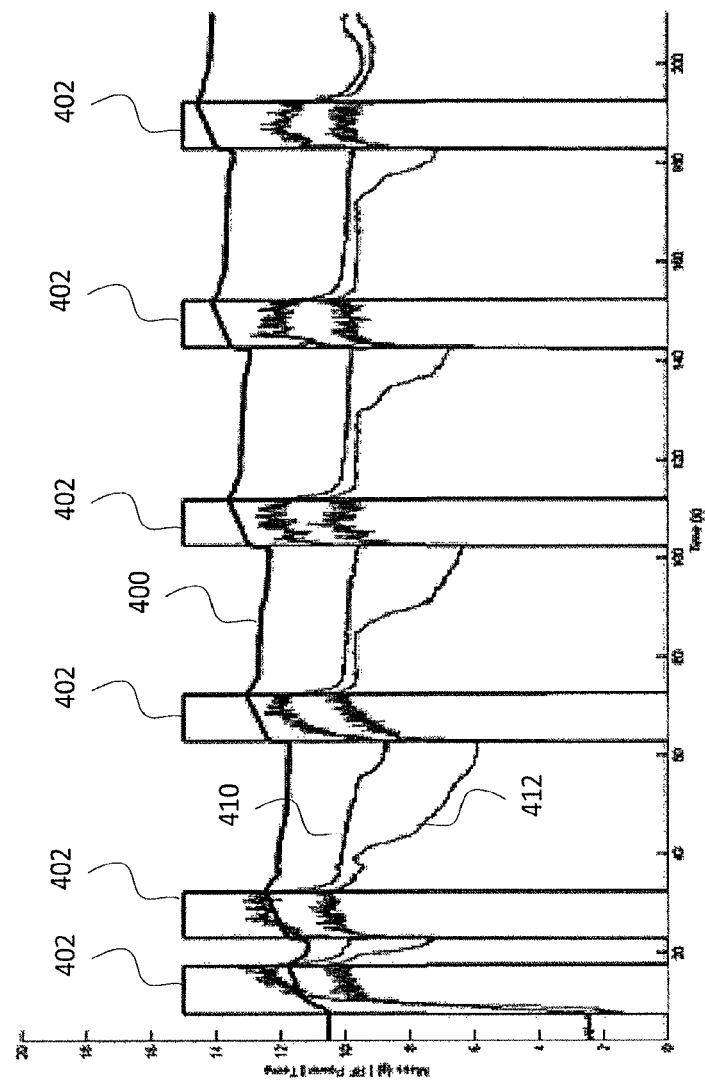
FIG. 4 illustrates the mass drawback that occurs when an idle process is not activated.
Figure 5:
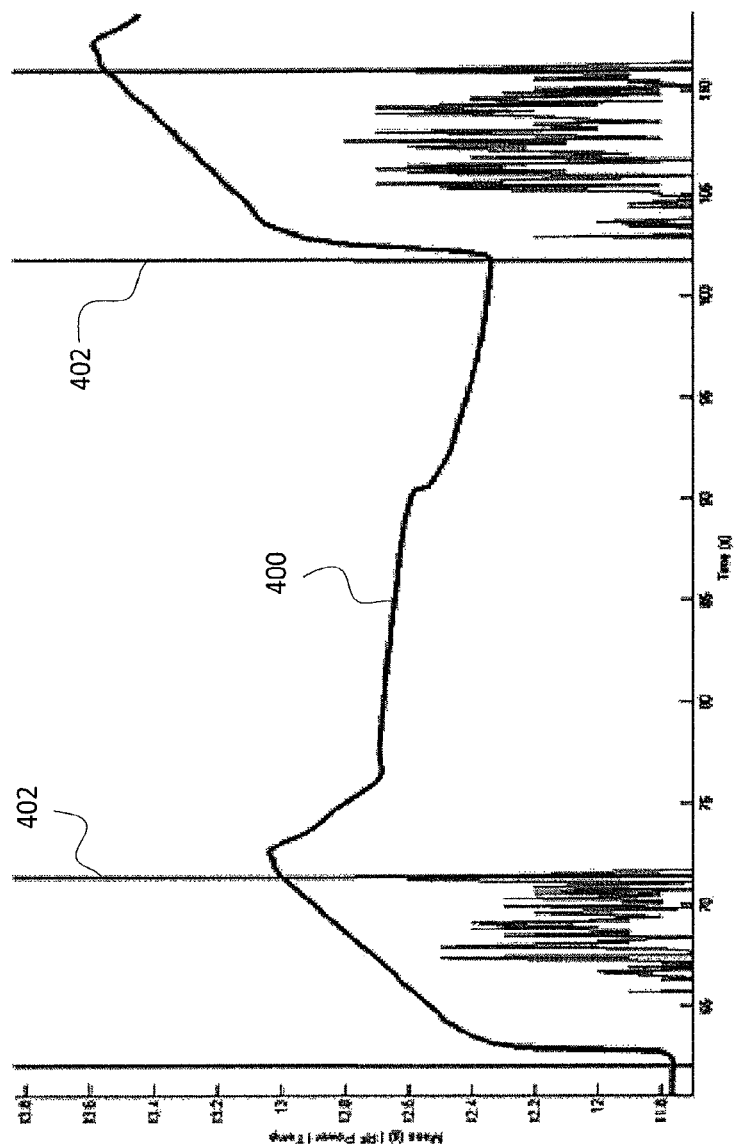
FIG. 5 is a close-up view of the chart of FIG. 4.
Figure 6:
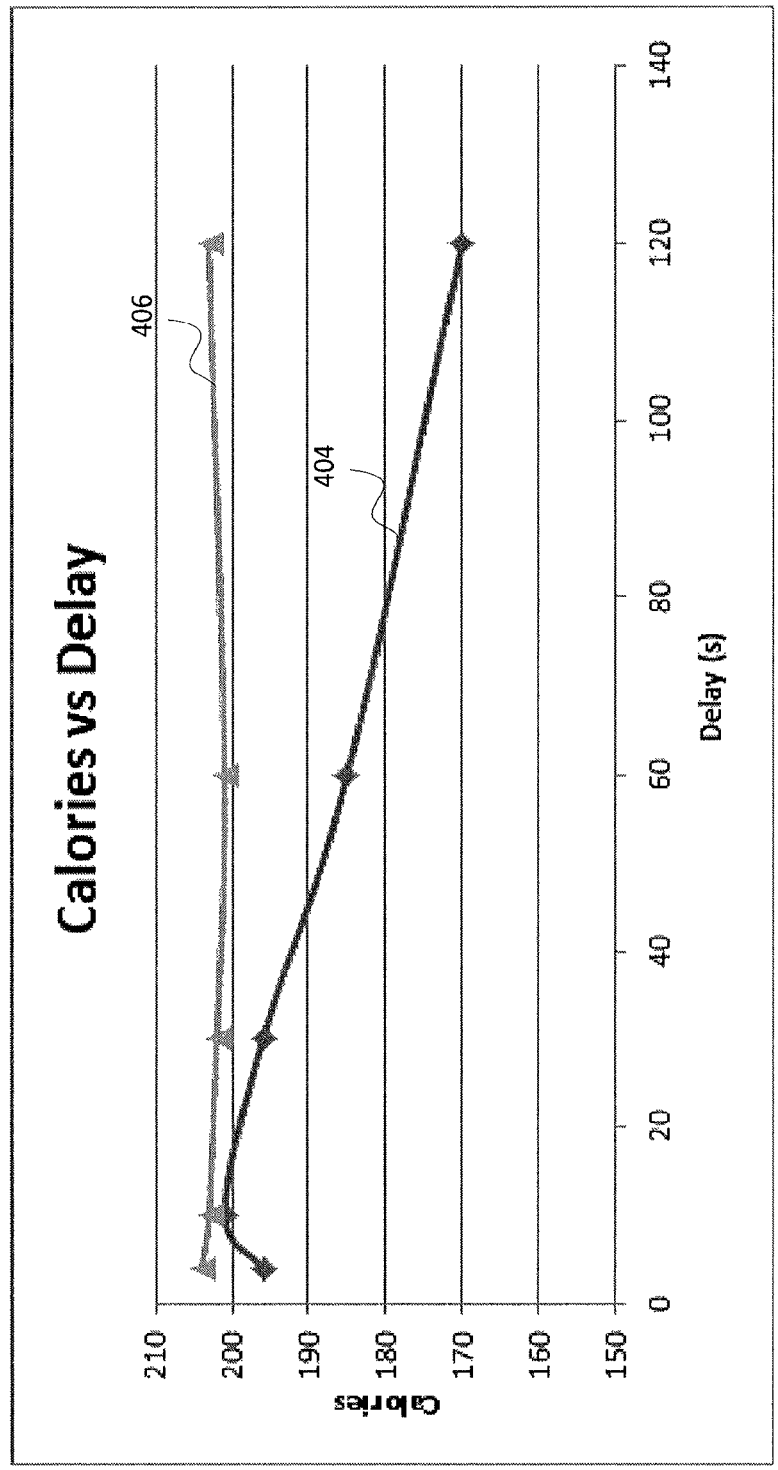
FIG. 6 illustrates the difference in calories delivered when an idle process is on vs. off.
Figure 7:
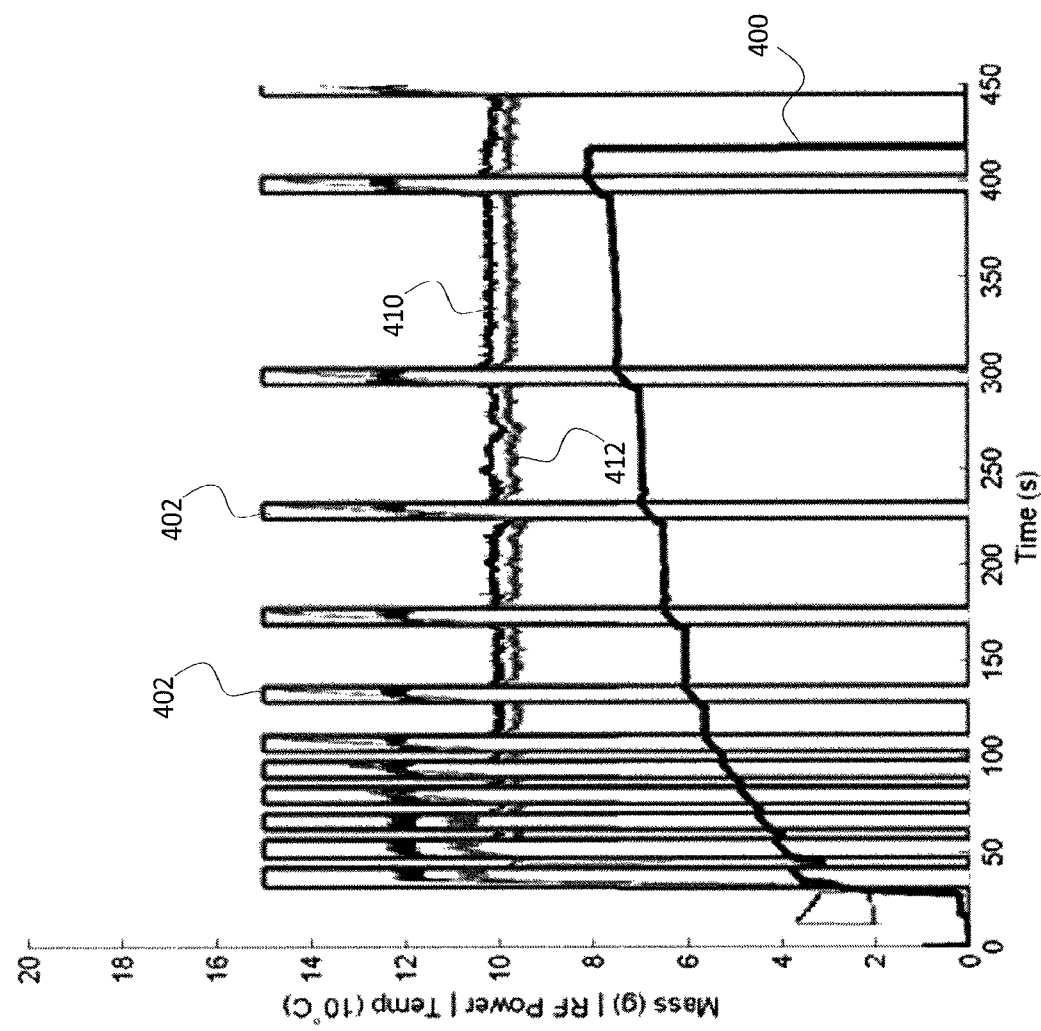
FIG. 7 illustrates the temperatures of the system vs. mass drawback when the idle process is activated.

FIG. 3 provides a cross sectional view of elongate shaft 102 of vapor delivery system 100 from FIGS. 1-2. Lumen 148 can be configured to accommodate the vapor delivery needle described above and in FIGS. 1-2, to allow for the vapor delivery needle to be advanced from the shaft during vapor delivery. Lumen 111 formed within tube 112 can have a diameter ranging from about 2 to 5 mm for accommodating various endoscopes or cameras 118, while at the same time providing an annular space 138 for allowing an irrigation fluid to flow within lumen 111 and outwardly from the shaft into the urethra. As can be seen in FIG. 3, the lumen 111 is dimensioned to provide a space 138 for fluid irrigation flow around the endoscope 118. In some embodiments, the annular space 138 can be a separate concentric lumen around the endoscope for irrigation fluid flow. The annular space 138 allows for flow of irrigation fluid from the vapor delivery system into the urethra, and also provides cooling to the shaft and adjacent urethra when vapor is delivered from the vapor delivery needle (disposed in lumen 148) into tissue. Material 144 in FIG. 3 can conduct heat from the vapor delivery needle to the irrigation fluid flowing in annular space 138, or alternatively, can conduct cooling from the irrigation fluid to the vapor delivery needle, to prevent over-heating of the patient (particularly the urethra) during vapor therapy.

During vapor ablation therapy, referring to FIGS. 1-3, vapor travels from the vapor source 250 to the patient through the vapor delivery needle 106. The length of the vapor delivery needle allows for some condensation of the vapor as it travels through the needle towards the vapor delivery ports. Condensation of vapor in the vapor delivery needle can result to in many undesirable behaviors of the vapor delivery system. This issue can be particularly problematic between doses of vapor therapy. For instance, as the vapor in the vapor delivery needle starts to condense following a vapor therapy shot or dose, the volume of vapor is reduced to the volume of water, and therefore a vacuum is created in the needle. This vacuum can then pull material, such as blood, tissue, or fluid, from the urethra into the needle tip through the vapor delivery ports. Upon reactivating the therapy, this material is ejected from the needle prior to new vapor being delivered into the tissue. The ejected material can exit the needle at high velocities, and is often observed as "spitting water" in the tissue or as it exits the needle. Additionally, materials drawn back into the needle can potentially plug vapor delivery ports and/or the vapor delivery needle between vapor shots or doses, which can result in uneven distribution of vapor and therefore mis-shaped lesions.

Furthermore, the amount of cooling and condensation that takes place between therapy shots is a function of time between shots, and therefore contributes to variability in the following therapy shot. If the system is allowed to sit, and cool, for an extended period of time, the following therapy shot may produce fewer calories than if consecutive shots were applied quickly.

According to one embodiment, to mitigate the drawback and cooling issues, an "Idle" feature can be implemented in the vapor delivery system 100 of FIGS. 1-3. When the idle feature is enabled, the vapor delivery system can be configured via the controller 255 to pump a very small amount of vapor (e.g., 0.1-0.3 ml/min) from the vapor source 250 through the vapor delivery needle 106 at all times between therapy shots. The vapor can be pumped through the internal lumen of the needle and out of the vapor delivery ports. Furthermore, the vapor source can be maintained at a heated temperature, such as 90-100 degrees Celsius, and preferably 100 degrees Celsius, to prevent the vapor field from collapsing. This idle feature results in a constant positive pressure field in the vapor delivery needle 106, and prevents any vacuum that might draw material into the needle. Furthermore, this allows for minimal "spitting" of water upon initiation of following therapy shots, and reduces shot to shot variably in calorimetric output.

In some embodiments, the idle feature is first activated after the system has been primed, and the doctor has performed one test therapy shot outside of the patient. Following this initial activation, the idle feature can be always on between therapy shots. In one embodiment, idle is only interrupted if the system determines there is a problem in the heating element or in the water path in the needle. This may be evident given abnormal temperature behavior in the heating coil, or given high pressure readings. In one embodiment, software could allow for manual activation and deactivation of the idle feature.

FIG. 4 shows the mass drawback that occurs between treatments when the idle feature is disabled. For this measurement, the vapor delivery system was mounted above a small container of water resting on a gram scale. The vapor delivery needle was held under the water level at all times, and the change in weight of the container measured the weight of vapor injected into the water, and the suctioning of water back into the delivery needle during the time between vapor injections. Mass line 400 indicates the weight of the container. The mass line 400 is seen to decrease between therapy shots 402, indicating that water, fluid, blood, or tissue would be drawn back into the vapor delivery needle between therapy shots. The vapor outlet temperature 410 and vapor source temperature 412 are also shown plotted in FIG. 4.

FIG. 5 is zoomed into the time between the third and fourth treatment shots 402 of FIG. 4. During the 30 seconds between these two shots, approximately 0.7 mL of fluid is drawn back into the tool, which is a typical level of drawback when the idle feature is disabled. The sharp rise in mass at the beginning of the treatment represents this fluid being rapidly expelled from the vapor delivery system.

FIG. 6 demonstrates the effect of the idle feature on the consistency of calories delivered to tissue with the vapor shots. With the idle feature turned off or disabled (line 404), the measured calories vary within approximately a 30 calorie range, depending on the delay since the previous therapy shot. With the idle feature turned on or enabled (line 406), the measured calories are very consistent, and varies no more than 5 calories regardless of the delay between therapy shots.

Drawback testing was conducted on 30 delivery tools for a total of 44 trials (one batch was tested once with old therapy setting and then again with new therapy settings but idle settings remained the same throughout). This testing involved suspending the vapor delivery system and shooting it into a cup of water on a scale. The mass on the scale can then be used to determine if water/vapor is being expelled from the tool (increase in mass) or drawn back into the tool (decrease in mass). This mass data was logged and then plotted on top of the generator data such as temperature and RF power. FIG. 7 shows an example of this plot for one vapor delivery system with idle active between therapy shots. As can be seen, the mass (line 400) generally increases slightly between therapy shots 402, indicating that very little, if any, water is being drawn back into the vapor delivery needle of the system. Additionally, the vapor source temperature 410 and outlet temperature 412 remain very consistent during Idling.

Table I shows some additional metrics for the data represented above. Each table contains the minimum, mode, and maximum of each parameter, as well as the percentage of data points that fall within 5 units (° C. or psi) of the mode and within 10 units of the mode.

TABLE I

Metrics of Temperature and Pressure Data during Idling

| | Units | Data Excluded (s) | Min | Mode | Max | % in Mode +/− 5 | % in Mode +/− 10 |
|---|---|---|---|---|---|---|---|
| Coil | ° C. | 0 | 90 | 102 | 153 | 90.6% | 97.0% |
| Temp | | 4 | 90 | 102 | 138 | 94.8% | 99.0% |
| | | 30 | 90 | 102 | 119 | 97.3% | 99.9% |
| Outlet | ° C. | 0 | 69 | 98 | 219 | 74.8% | 77.8% |
| Temp | | 4 | 69 | 98 | 218 | 82.7% | 85.45% |
| | | 30 | 69 | 98 | 128 | 99.7% | 99.9% |
| Water | psi | 0 | -0.5 | 0 | 28.1 | 99.5% | 99.6% |
| Pressure | | 4 | -0.5 | 0 | 10.4 | 100% | 100% |
| | | 30 | -0.5 | 0 | 7.0 | 100% | 100% |

Overall, the results look very good. The 0 second delay data (Table I) shows that there are no instances of temperatures or pressures that are outside of the bounds that are monitored during the idle process.

The 4 second delay data (Table I) shows the possible temperature and pressure conditions that could be present when a treatment is activated. For vapor generator temperature, 99% of the data points fall within 10° C. of the mode (102° C.). For water pressure, 100% of the data points fall within 10 psi of the mode (0 psi). For outlet temperature, there is a bit more spread, with only 85% of the data falling within 10° C. of the mode (98° C.) and temperatures reaching as high as 218° C.

By excluding the high temperatures and pressures that sometimes linger following a treatment, the 30 second delay data (Table I) show the temperature and pressure conditions that are created by the idle process as opposed to just those experienced during idling. There are no instances of the temperature or pressure increasing or decreasing substantially in an uncontrolled and undesirable fashion. For all three parameters, over 97% of the data points fall within 5 units of the mode and 99.9% of the data points fall within 10 units of the mode.

The use of the idle feature between therapy vapor shots may be combined with control mechanisms during therapy and/or during idle to further insure consistent energy delivery from shot to shot. For example, the power output of the RF generator or source that creates the vapor may be servo controlled to a constant value so that the energy delivered to the heating element is constant and independent of impedance changes in the delivery tool.

In another embodiment, a parameter of the vapor heating element may be monitored and controlled to a fixed value. In one example, the temperature of the inductive coil of the vapor source in which vapor is generated is monitored and controlled at a constant value during therapy by adjusting RF power in real time. The vapor heating element temperature may also be monitored during idle, and controlled to a set temperature, for example 100° C. A preferred method for monitoring temperature may be the measurement of heating element impedance (equal to rms Voltage divided by rms current at the RF generator output). Impedance of the heating element increases with temperature, and may more accurately represent the average temperature of the heating element than a thermometer (e.g., thermocouple) measuring temperature at one point on the heating element. In this embodiment, RF power is adjusted to maintain impedance at one set point during therapy shots and at a second set point during idle.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A vapor delivery system, comprising:
a shaft configured to be inserted into a urethra of a patient;
a vapor delivery needle disposed within the shaft and including a lumen in fluid communication with a vapor delivery port;
a vapor source in fluid communication with the lumen of the vapor delivery needle; and
an electronic controller configured to:
deliver an ablative treatment dose of vapor from the vapor source through the vapor delivery port of the vapor delivery needle; and
automatically deliver a non-ablative interim flow of the vapor from the vapor source through the vapor delivery port of the vapor delivery needle to introduce positive pressure in the lumen of the vapor delivery needle after delivery of the treatment dose, wherein an amount of the vapor in the interim flow is less than an amount of the vapor in the treatment dose.

2. The system of claim 1, wherein a flow rate of the interim flow of the vapor ranges from approximately 0.1 ml/minute to 0.3 ml/minute.

3. The system of claim 1, wherein the treatment dose is a first treatment dose and wherein the controller is further configured to, after delivering the interim flow of the vapor, deliver a second treatment dose of the vapor from the vapor source through the vapor delivery needle.

4. The system of claim 3, wherein the positive pressure is configured to exist for an entirety of a time between the delivery of the first treatment dose of the vapor and the delivery of the second treatment dose of the vapor.

5. The system of claim 4, wherein the positive pressure is configured to vary over at least a portion of the entirety of the time.

6. The system of claim 1, wherein the vapor source comprises a vapor generator, and wherein the controller is further configured to:
monitor a parameter of the vapor generator;
perform a comparison of the parameter to a predetermined value; and
adjust the vapor generator based on the comparison of the parameter to the predetermined value.

7. The system of claim 6, wherein the parameter is a temperature of the vapor emitted from the vapor generator.

8. The system of claim 7, wherein the vapor generator includes a heating element, and wherein the temperature of the vapor emitted from the vapor generator is monitored by measuring an impedance of the heating element.

9. The system of claim 6, wherein the predetermined value is a first predetermined value, and wherein the controller is further configured to:
perform a comparison of the parameter to the first predetermined value during the delivery of the treatment dose of the vapor;
perform a comparison of the parameter to a second predetermined value during the delivery of the interim flow of the vapor; and
adjust the vapor generator based on the comparison of the parameter to the first predetermined value or the second predetermined value.

10. A vapor delivery system, comprising:
a shaft configured to be inserted into a urethra of a patient;
a vapor delivery needle disposed within the shaft and including a lumen in fluid communication with a vapor delivery port;

a vapor source fluidly coupled to the lumen of the vapor delivery needle; and an electronic controller configured to:
deliver a first ablative treatment dose of vapor from the vapor source through the vapor delivery port of the vapor delivery needle;
automatically deliver a non-ablative interim flow of the vapor from the vapor source through the vapor delivery port of the vapor delivery after delivering the first treatment dose of the vapor, the interim flow of the vapor including a lesser quantity of the vapor than a quantity of the first treatment dose; and
deliver a second ablative treatment dose of the vapor from the vapor source through the vapor delivery port of the vapor delivery needle after delivering the interim flow of the vapor.

11. The system of claim 10, wherein a flow rate of the interim flow of the vapor ranges from approximately 0.1 ml/minute to 0.3 ml/minute.

12. The system of claim 10, wherein the controller is further configured to sustain a non-negative pressure in the lumen of the vapor delivery needle between the delivery of the first treatment dose and the delivery of the second treatment dose.

13. The system of claim 10, wherein the vapor source includes a vapor generator, and wherein the controller is further configured to:
monitor a parameter of the vapor generator;
perform a comparison of the parameter to a predetermined value; and
adjust the vapor generator based on the comparison of the parameter to the predetermined value.

14. The system of claim 13, wherein the parameter is a temperature of the vapor emitted from the vapor generator.

15. The system of claim 14, wherein the vapor generator includes a heating element, and wherein the temperature of the vapor emitted from the vapor generator is monitored by measuring an impedance of the heating element.

16. The system of claim 13, wherein the predetermined value is a first predetermined value, and wherein the controller is further configured to:
perform a comparison of the parameter to the first predetermined value during the delivery of the first treatment dose of the vapor and the second treatment dose of the vapor; and
perform a comparison of the parameter to a second predetermined value during the delivery of the interim flow of the vapor; and
adjust the vapor generator based on the comparison of the parameter to the first predetermined value or the second predetermined value.

17. A vapor delivery system, comprising:
a shaft configured to be inserted into a urethra of a patient;
a vapor delivery needle disposed within the shaft and comprising a lumen in fluid communication with a vapor delivery port;
a vapor source in fluid communication with the vapor delivery port of the vapor delivery needle; and
an electronic controller configured to:
deliver an ablative treatment dose of vapor from the vapor source through the vapor delivery port of the vapor delivery needle; and
automatically deliver a non-ablative flow of the vapor after delivering the treatment dose of the vapor, the non-ablative flow of the vapor having a flow rate ranging from approximately 0.1 ml/minute to 0.3 ml/minute.

18. The system of claim 17, wherein the vapor source comprises a vapor generator, and wherein the controller is further configured to:
monitor a parameter of the vapor generator;
perform a comparison of the parameter to a predetermined value; and
adjust the vapor generator based on the comparison of the parameter to the predetermined value.

19. The system of claim 18, wherein the parameter is a temperature of the vapor emitted from the vapor generator, wherein the vapor generator includes a heating element, and wherein the temperature of the vapor emitted from the vapor generator is monitored by measuring an impedance of the heating element.

20. The system of claim 17, wherein the vapor source includes a vapor generator, and wherein the controller is further configured to:
monitor a parameter of the vapor generator;
perform a comparison of the parameter to a first predetermined value during the delivery of the treatment dose of the vapor;
perform a comparison of the parameter to a second predetermined value during the delivery of the flow of the vapor; and
adjust the vapor generator based on the comparison of the parameter to the first predetermined value or the second predetermined value.

* * * * *